(12) United States Patent
Tsai

(10) Patent No.: US 7,365,177 B2
(45) Date of Patent: Apr. 29, 2008

(54) RECOMBINANT PLASMID EXPRESSING TWO FLUORESCENCE GENES

(75) Inventor: Huai-Jen Tsai, 2th Fl., No. 2-6, ChowZhou St., Taipei (TW)

(73) Assignees: Taikong Corporation, Taipei (TW); Huai-Jen Tsai, Taipei (TW)

( * ) Notice: Subject to any disclaimer, the term of this patent is extended or adjusted under 35 U.S.C. 154(b) by 317 days.

(21) Appl. No.: 10/759,268

(22) Filed: Jan. 20, 2004

(65) Prior Publication Data

US 2004/0216179 A1 Oct. 28, 2004

(30) Foreign Application Priority Data

Apr. 23, 2003 (TW) ............... 92109420 A

(51) Int. Cl.
C07H 21/02 (2006.01)
C07H 21/04 (2006.01)
A01K 67/027 (2006.01)

(52) U.S. Cl. .................. 536/23.1; 536/24.1; 800/20

(58) Field of Classification Search .................. None
See application file for complete search history.

(56) References Cited

OTHER PUBLICATIONS

Higashijima, S., 1997, High-frequency generation of transgenic zebrafish which reliably express GFP in whole muscles or the whole body using promoters of zebrafish origin, Dev. Biol., 192:289-299.*

Ju, B et al., 1999, Faithful expressionof green fluorescent protein (GFP) in transgenic zebrafish embryos under control of zebrafish promoters, Developmental Genetics, 25:158-167.*

Yu, et al, Nov. 2002, Lentiviral vectors with dual promoters transfer high-level expression of multiple genes in human hematpoietic progenitor cells, Blood, 100 Abstract No. 1698.*

Thavathiru, E and Das, GM. 2001, Activation od pRL-TK by 12S E1A oncoprotein:Drawbacks od using an internal reference reporter in transcription assays. Biotechniqques, 31:528-532.*

Flanagan, WM et al, 1987, A bifunctional reporter plasmid for the simultaneous transient expression assau of two herpes simplex virus promoters, Virus Gene, 1:61-71.*

Jyh-Yih Chen, et al., Isolation and Characterization of Tilapia (*Oreochromismossambicus*) Insulin-Like Growth Factors Gene and Proximal Promoter Region, DNA and Cell Biology, vol. 17, No. 4, 1998, Mary Ann Liebert, Inc. p. 359-376.

Keiko Hamada, et al., Usefulness of the medaka β-action promoter investigated using a mutant GFP reporter gene in transgenic medaka (*Oryzias latipes*), Molecular Marine Biology and Biotechnology (1998) 7(3), 173-180.

Jennifer Barnett Moss, et al., "Green Fluorescent protein marks skeletal muscle I murine cell line and zebrafish", Gene. 173 (1996) 89-98.

* cited by examiner

*Primary Examiner*—Valarie Bertoglio
(74) *Attorney, Agent, or Firm*—Harness, Dickey and Pierce, P.L.C.

(57) ABSTRACT

Recombinant plasmids comprising (a) a ubiquitous promoter, (b) one fluorescent gene, the gene being operably liked to and inserted downstream of the ubiquitous promoter, (c) a skin-specific or muscle-specific promoter, and (d) another fluorescent gene, the gene being operably linked to and inserted downstream the skin-specific or muscle specific promoter. The ubiquitous promoter and the skin-specific or muscle promoter have the adverse directional property and the ubiquitous promoter and the skin-specific or muscle-specific promoter are located upstream of the fluorescent gene and the another fluorescent gene respectively so as to have the directional property which permits transcription of the genes. Host cells, transgenic fish harboring the plasmid of the invention and methods of producing a transgenic fish can be made with the plasmids of the invention.

1 Claim, 2 Drawing Sheets

RECOMBINANT PLASMID EXPRESSING TWO FLUORESCENCE GENES

BACKGROUND OF THE INVENTION

1. Field of the Invention

The present invention relates to a recombinant plasmid, a method of producing a transgenic fish, a host cell and transgenic animal containing it.

2. Description of the Prior Art

Transgenic fish studies make use of genes that are driven by both heterologous and homologous sources of regulatory element, and originate from constitutive or tissue-specific expression genes. Control elements include genes from antifreeze protein, mouse metallothionein, chicken δ-crystalline, carp β-actin, salmon histone H3 and carp α-globin and so on. However, there are important drawbacks to the use of these DNA elements in transgenic fish, including low expression efficiency and the mosaic expression of transgene patterns.

The microinjection into mekada eggs of lac reporter gene driven by the mekada β-actin promoter results in the transient expression of the lacZ gene, even in the F1 generation, though expression is low and highly mosaic. Hamada et al. reported a similar result in medaka embryos derived from eggs microinjected with green fluorescence protein fused with the medaka β-actin promoter (Hamada et al., 1998, Mol Marine Biol Biotechnol 7: 173-180).

Chi-Yuan Chou et al. disclosed a DNA construct flanked at both ends by ITRs to increase the efficient expression of transgenic genes in medaka. A uniform transgene expression was achieved in the F0 and the following two generations (Chi-Yuan Chou et al., 2001, Transgenic Research 10: 303-315). Moreover, Chung-Der Hsiao et al. indicated that the incorporation of AAV-ITPs into transgenes results in uniform gene expression in the F0 generation and stable transmission of transgenes in zebrafish (Chung-Der Hsiao et al., 2001, Developmental Dynamics 220:323-336).

The zebrafish, Danio rerio, is a new model organism for vertebrate developmental biology. As an experimental model, the zebrafish offers several major advantages such as easy availability of eggs and embryos, tissue clarity throughout embryogenesis, external development, short generation time and easy maintenance of both the adult and the young.

The known fluorescent genes such as GFP gene (including EGFP gene) have been introduced into zebrafish by using various gene promoters, including rat myosin light-chain enhancer (Moss, J. B. et al., Green fluorescent protein marks skeletal muscle in murine cell lines and zebrafish. Gene 173, 8998, 1996), zebrafish and tilapia insulin-like growth factor I promoter (Chen, J. Y et al., Isolation and characterization of tilapia (Oreochromis mossambicus) insulin-like growth factors gene and proximal promoter region (DNA Cell Biol. 17,359-376, 1998). All of these transgenic experiments aim at either developing a GFP transgenic system for gene expression analysis or at testing regulatory DNA elements in gene promoters.

WO0049150 discloses a fluorescent transgenic ornamental fish expressed by single fluorescent gene such as GFP. However, no fishes expressing two or more fluorescent genes uniformly and stably are developed.

SUMMARY OF THE INVENTION

The present invention relates to a recombinant plasmid, comprising (a) a ubiquitous promoter, (b) one fluorescent gene, said gene being operably linked to and inserted downstream of said ubiquitous promoter, (c) a skin-specific or muscle-specific promoter, and (d) another fluorescent gene, said gene being operably linked to and inserted downstream of said skin-specific or muscle-specific promoter, wherein the ubiquitous promoter and the skin-specific or muscle-specific promoter have the adverse directional property and the ubiquitous promoter and the skin-specific or muscle-specific promoter are located upstream of said fluorescent gene and said another fluorescent gene respectively so as to have the directional property which permits transcription of said genes.

The present invention also relates to a host cell, comprising the plasmid of the invention.

The present invention further relates to a method of producing a transgenic fish, said method comprising:
a) introducing the plasmid of the invention into a fish egg cell or embryonic cell, and
b) allowing the egg cell or embryonic cell to develop into a fish, wherein the plasmid of the invention is introduced into the genome of the fish.

The present invention further relates to a method of producing a transgenic fish that expresses two fluorescent genes simultaneously, said method comprises the following steps:
a) restricting the plasmid of the invention with restriction enzymes in appropriate restriction sites to obtain two plasmid fragments I and II, wherein said plasmid I contains the fragments a) and b) as defined in the plasmid of the invention and said plasmid II contains the fragments c) and d) as defined in the plasmid of the invention;
b) introducing each of said plasmids A and B of step a) into fish egg cell or embryonic cell respectively;
c) allowing said fish to express the plasmids I and II simultaneously.

The present invention also relates to a transgenic animal, which is transformed with the plasmid of the invention.

DETAILED DESCRIPTION OF THE INVENTION

Figure 1:
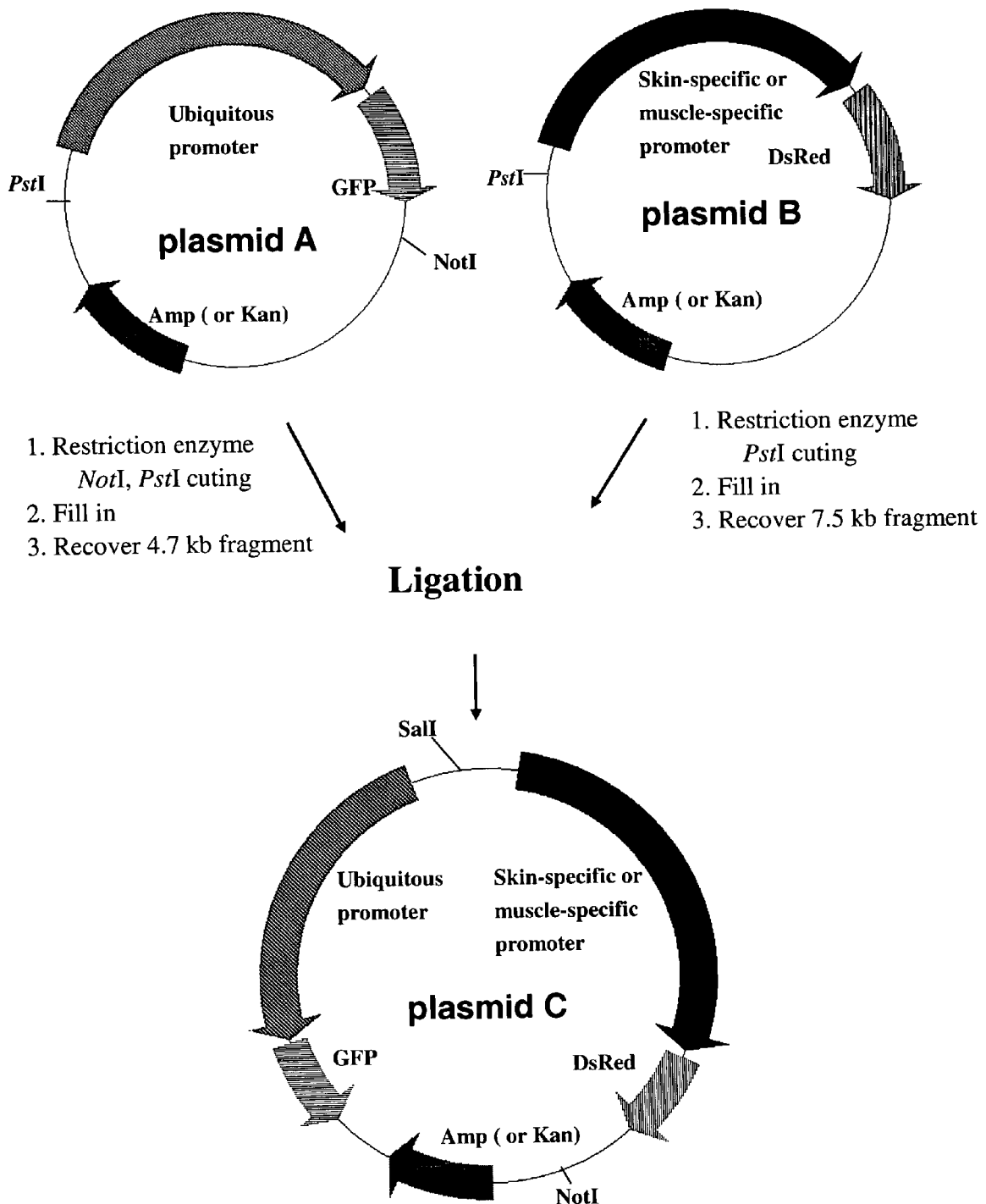
FIG. 1 shows a scheme of producing plasmid C by ligating plasmid A and plasmid B.
Figure 2:
FIG. 2 shows the photograph of a transgenic fish expressing two fluorescent genes.

The present invention provides a recombinant plasmid for introducing two or more (such as green and red fluorescent) genes into fishes. The fishes exhibit uniform and strong fluorescence under general light sources.

The present invention provides a recombinant plasmid, comprising (a) a ubiquitous promoter, (b) one fluorescent gene, said gene being operably linked to and inserted downstream of said ubiquitous promoter, (c) a skin-specific or muscle-specific promoter, and (d) another fluorescent gene, said gene being operably linked to and inserted downstream of said skin-specific or muscle-specific promoter, wherein the ubiquitous promoter and the skin-specific or muscle-specific promoter have the adverse directional property and the ubiquitous promoter and the skin-specific or muscle-specific promoter are located upstream of said fluorescent gene and said another fluorescent gene respectively so as to have the directional property which permits transcription of said genes.

As used herein, the terms "upstream" and "downstream" mean that, when the reference direction is defined as the direction leading from the initiation codon to the termination codon of the fluorescent gene, the side of a point lying in the same direction as the reference direction is "downstream" of the point and the side lying in the direction opposite to the reference direction is "upstream" of the point.

According to the invention, the ubiquitous promoter is used to drive the expression of fluorescence gene in the plasmid of the invention. The ubiquitous promoter and the skin-specific or muscle-specific promoter have the adverse directional property and the ubiquitous promoter is located upstream of said fluorescent gene so as to have the directional property which permits transcription of the fluorescent gene. Preferably, the ubiquitous promoter is selected from the group consisting of β-actin, elongation-1-α, 18 S-rDNA and 5 S-rDNA.

According to the invention, the skin-specific or muscle-specific promoter is used to derive the expression of fluorescent gene. The skin-specific or muscle-specific promoter is located upstream of said fluorescent gene so as to have the directional property which permits transcription of the fluorescent gene. Preferably, the skin-specific or muscle-specific promoter is selected from the group consisting of α-actin, troponin T, Troponin C, myosin heavy chain, cytokarotin type II C and S-100.

According to the invention, any kind of fluorescent genes can be inserted downstream of the promoters of the plasmid of the invention. Preferably, the fluorescent genes are selected from the group consisting of green, red, yellow and blue fluorescent genes. The fluorescent genes are commercial available; for example, which can be obtained from Clonteh Laboratories, Inc., Lightools Research and BD Biosciences Pharmingen, etc. More preferably, the fluorescent genes are selected from the group consisting of green and red fluorescent genes.

Hiroshi Otsuki et al. indicated that green fluorescence was observed whole part of rice plant including calli when using the ubiquitous promoter (Hiroshi Otsuki, Jan. 12-16, 2002, Plant, Animal & Microbe Genomes X Conference). According to the invention, the green fluorescent gene is operably linked to and inserted downstream of said ubiquitous promoter of the invention. The green fluorescence protein (GFP) was originally isolated from the jellyfish, Aequorea victoria, and is commercially available. GFP emits bright green light when simply exposed to UV or blue light, unlike other bioluminescent reporters. The emission of green light is due to the transfer of energy from the photoprotein, aequorin, of the organism to GFP. GFP is a 238 amino acid protein with a molecular weight of 28 kDa and has a major absorption peak at 395 nm and a minor peak at 470 nm with a single emission peak at 509 nm. Advantageously, its fluorescence is species-independent and requires no substrate, cofactor, or additional proteins for illuminating green light. GFP has been successfully expressed in several host organisms and cells such as E. coli, yeast, mammalian cells, insect cells, and plant cells.

According to the invention, the red fluorescent gene can be purchased from BD Bioscience Clontech. In the embodiment of the invention, pDsRed2-1 is used as the source of the red fluorescent gene. pDsRed2-1 encodes DsRed2, a DsRed variant engineered for faster maturation and lower non-specific aggregation. Derived from the Discosoma sp. red fluorescent protein (drFP583; Matz, M. V., et al. (1999) Nature Biotech. 17:969-973.), DsRed2 contains a series of silent base-pair changes that correspond to human codon-usage preferences for high expression in mammalian cells (Haas, J., et al. (1996) Curr. Biol. 6:315-324.). In mammalian cell cultures when DsRed2 is expressed constitutively, red-emitting cells can be detected by fluorescence microscopy within 24 hours of transfection. Large insoluble aggregates of protein, often observed in bacterial and mammalian cell systems expressing DsRed1, are dramatically reduced in cells expressing DsRed2. The faster-maturing, more soluble red fluorescent protein is also well tolerated by host cells; mammalian cell cultures transfected with DsRed2 show no obvious signs of reduced viability—in those cell lines tested, cells expressing DsRed2 display the same morphology (e.g., adherence, light-refraction) and growth characteristics as non-transfected controls. pDsRed2-1 is a promoterless DsRed2 vector that can be used to monitor transcription from different promoters and promoter/enhancer combinations inserted into the multiple cloning site (MCS). Sequences upstream of DsRed2 have been converted to a Kozak consensus translation initiation site (Kozak, M. (1987) Nucleic Acids Res. 15:8125-8148.) to increase translation efficiency in eukaryotic cells. SV40 polyadenylation signals downstream of the DsRed2 gene direct proper processing of the 3' end of the DsRed2 mRNA. The vector backbone contains an SV40 origin for replication in mammalian cells expressing the SV40 T antigen, a pUC origin of replication for propagation in E. coli, and an f1 origin for single-stranded DNA production. A neomycin-resistance cassette (Neo') allows stably transfected eukaryotic cells to be selected using G418. This cassette consists of the SV40 early promoter, the neomycin/kanamycin resistance gene of Tn5, and polyadenylation signals from the Herpes simplex virus thymidine kinase (HSV TK) gene. A bacterial promoter upstream of the cassette expresses kanamycin resistance in E. coli.

According to the invention, the recombinant plasmid is constructed by combining the plasmid containing ubiquitous promoter and one fluorescent gene, and the plasmid containing skin-specific or muscle-specific promoter and another fluorescent gene, using standard molecular techniques known in the art. In one embodiment of the invention, the plasmid containing ubiquitous promoter and green fluorescent gene is cleaved by restriction enzyme to obtain a 4.7 kb fragment. The plasmid containing skin-specific or muscle-specific promoter and red fluorescent gene is cleaved by restriction enzyme to obtain a 7.5 kb fragment. The resulting 4.7 kb fragment and 7.5 kb fragment are fused through ligation procedures.

The present invention provides a host cell, which comprises the plasmid of the invention. According to the invention, a number of host systems may be utilized to contain the plasmid of the invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors; plant cell systems transformed with virus expression vectors or with bacterial expression vectors; or animal cell systems.

The present invention provides a transgenic animal, which is transformed with the plasmid of the invention. According to the invention, the transgenic animals may be any convenient animals, such as non-human mammal, for example as used in laboratory test procedures such as rodents and fish. The transgenic animals of the invention are conveniently obtained by introducing into animals the plasmid of the invention using conventional and convenient genetic manipulation techniques such as by microinjection or by infection with a recombinant vector. The gene may be directly or indirectly introduced into a cell or all the cells of an animal by introduction into a precursor of the cell. The genetic manipulation techniques include classical crossbreeding, in vitro fertilization, introduction of a recombinant DNA molecule, which may be integrated within a chromosome or may be extrachromosomally replicating DNA. Preferably, the transgenic animal is transgenic fish. More preferably, the transgenic fish is selected from the group consisting of mekada, zebrafish, discus, goldfish, killifish, cichlid, guppy, arowana, koi, show betta and other ornamental fish. According to the invention, the transgenic fish: of the invention expresses a color mixed with green and red colors.

According to one embodiment of the invention, the plasmid of the invention can be used in the production of the fish expressing single fluorescence, mixed fluorescence and different fluorescence simultaneously. For expressing single fluorescent gene, the plasmid of the invention is restricted with appropriate restriction enzymes to generate the plasmid fragments containing single fluorescent gene. The resulting single plasmid is introduced into fish egg cells or embryonic cells to obtain fish expressing single fluorescent gene. For expressing the mixed fluorescence, the plasmid of the invention is introduced into fish egg or embryonic cells to obtain fish expressing mixed fluorescence. For expressing different fluorescence simultaneously, the different pasmids containing different fluorescent genes are introduced into fish egg cells or embryonic cells simultaneously to obtain fish expressing different fluorescent genes simultaneously.

Preferably, the plasmid of the invention can be used in the production of the fish expressing single green fluorescent gene, single red fluorescent gene, mixed green and red fluorescent gene or green and red fluorescent genes simultaneously. For the fish expressing green fluorescence, the plasmid of the invention is restricted with restriction enzyme in an appropriate site to obtain a plasmid containing a ubiquitous promoter and a green fluorescent gene operably linked to and inserted downstream of said ubiquitous promoter, and the resulting plasmid is introduced into eggs or embryos of fish to express the green fluorescence. For the fish expressing red fluorescence, the plasmid of the invention is restricted with restriction enzyme in an appropriate site to obtain a plasmid containing a skin-specific or muscle-specific promoter and a red fluorescent gene operably linked to and inserted downstream of said skin-specific or muscle-specific promoter, and the resulting plasmid is introduced into fish egg cells or embryonic cells to express the red fluorescence.

According to one preferred embodiment of the invention, the invention provides a method of producing a transgenic fish expressing mixed fluorescence, said method comprising a) introducing the plasmid of the invention into a fish egg cell or embryonic cell, and b) allowing the egg cell or embryonic cell to develop into a fish, wherein the plasmid of the invention is introduced into the genome of the fish to obtain the fish expressing mixed fluorescence. Preferably, the fluorescent genes are selected from the group consisting of green, red, yellow and blue fluorescent genes. More preferably, the fluorescent genes are selected from the group consisting of green and red fluorescent genes.

According to one preferred embodiment of the invention, the invention provides a method of producing a transgenic fish that expresses two different fluorescent genes simultaneously, said method comprises the following steps:

a) restricting the plasmid of claim 1 with restriction enzymes in appropriate restriction sites to obtain two plasmid fragments I and II, wherein said plasmid I contains the fragments a) and b) as defined in Claim 1 and said plasmid II contains the fragments c) and d) as defined in Claim 1;

b) introducing each of said plasmids A and B of step a) into fish egg cell or embryonic cell respectively;

c) allowing said fish to express the plasmids I and II simultaneously.

According to the invention, the fish produced from the method of the invention can express two different fluorescence simultaneously. The plasmid of the invention is restricted with restriction enzymes in appropriate sites to obtain two plasmids, wherein one plasmid contains a ubiquitous promoter and one fluorescent gene operably linked to downstream of said ubiquitous promoter and the another plasmid contains a skin-specific or muscle-specific promoter and another fluorescent gene operably linked to and inserted downstream of said skin-specific or muscle-specific promoter. Then, the resulting two plasmids are introduced into a fish respectively to express different fluorescent genes respectively. Preferably, the fluorescent genes are selected from the group consisting of green, red, yellow and blue fluorescent genes. More preferably, the fluorescent genes are selected from the group consisting of green and red fluorescent genes.

According to the preferred embodiment of the invention, the fish obtained from the method of the invention can exhibit red and green fluorescence simultaneously. Preferably, the fish obtained from the method of the invention can be further bred using techniques known in the art to obtain a fish expressing red and green fluorescence uniformly and stably.

The following examples are offered by way of illustration and not by way of limitation.

EXAMPLES

Example 1

Construction of Plasmid Including GFP Sequence

Isolation of skin-specific, muscle-specific and ubiquitously expressed zebrafish cDNA clones. cDNA clones were isolated and sequenced as described by Gong, Z. et al., (1997), Gene 201,87-98. Basically, random cDNA clones were selected from zebrafish embryonic and adult cDNA libraries and each clone was partially sequenced by a single sequencing reaction. The partial sequences were then used to identify the sequenced clones for potential function and tissue specificity.

Plasmid A was a structural view of a plasmid construct as illustrated in FIG. 1. GFP was driven by the ubiquitous promoter. After plasmid was linearized by restriction enzymes of NotI and PstI, the sticky ends were blunted with dNTP by fill-in. A 4.7 kb fragment was recovered from the agarose gel. This plasmid illustrated the composition of the construct in accordance with the present invention.

Example 2

Construction of Plasmid Including Red Fluorescent Protein Sequence

Like Example 1, plasmid B was a structural view of a plasmid construct as illustrated in FIG. 1. DsRed was driven by the skin- or muscle-specific promoter. After plasmid was linearized by restriction enzyme of PstI, the sticky ends were blunted with dNTP by fill-in. A 7.5 kb fragment was recovered from the agarose gel. This plasmid illustrated the composition of the construct in accordance with the present invention.

Example 3

Construction of Plasmid by Ligating Plasmids A and B

Plasmid C was a structural view of a plasmid construct as illustrated in FIG. 1, representing the linearized fragment by restriction enzyme NotI or linearized fragments by restriction enzymes of NotI and SalI. This plasmid illustrated the compositions of the construct for gene transferring in accordance with the present invention.

Example 4

Production of Transgenic Zebrafish Expressing Two Fluorescent Genes

Zebrafish Breeding

A pool of male and female zebrafish are kept in a 60×20×30 cm glass aquarium set to 28.5° C. and a 14 hour photoperiod. The fish are fed with artemia twice a day. After that, several pairs of strong male and female zebrafish are selected and put in the 30×10×20 cm breeding cage equipped with a net for collecting eggs. For transgenic line, one pair of transgenic individual and wild-type are kept in a 22×14×13 cm tank.

Gene Transferring and Transgenic Founders' Screening

The fertilized eggs are collected with a plastic capillary and placed in a holder. A glass needle with 10 μm opening is filled with the linearized plasmid solution and mounts with mineral oil. The DNA sample is then microinjected into the one-celled fertilized eggs in a volume of 2-4 nl. The injected fertilized eggs are incubated in dishes containing low concentration of methylene blue solution and place in an incubator set to 28° C. Fluorescent expression of the embryos are observed in the third day by using a fluorescence microscope. Five days later, the fluorescent zebrafish are moved to an aquarium for rearing. Sexual maturation is achieved after 12 weeks.

Generation of Germ-line Transmission of Fluorescent Transgenic Zebrafish

The putative founders with the fluorescent expression are crossing with the wild-type strains. The transgenic F2 (the second progeny) are derived from inter-crossing between two fluorescent F1. The fluorescent expression can be observed in the fish over their entire lifespan.

Example 5

Potential Applications of Fluorescent Transgenic Fish

The fluorescent transgenic fish were used as ornamental fish in the market. Stably transgenic lines could be developed by breeding a GFP transgenic individual with a wild type fish or another transgenic fish. By isolation of more zebrafish gene promoters, such as eyespecific, bone-specific, tail-specific etc., and/or by classical breeding of these transgenic zebrafish, more varieties of fluorescent transgenic zebrafish could be produced.

Multiple color fluorescent fish may be generated by the same technique as blue fluorescent protein (BFP) gene, yellow fluorescent protein (YFP) gene and cyan fluorescent protein (CFP) gene were available from Clonetech. For example, a transgenic fish with GFP under an eye-specific promoter, BFP under a skin-specific promoter, and YFP under a muscle-specific promoter would show the following multiple fluorescent colors: green eyes, blue skin and yellow muscle. By recombining different tissue specific promoters and fluorescent protein genes, more varieties of transgenic fish of different fluorescent color patterns would be created. By expression of two or more different fluorescent proteins in the same tissue, an intermediate color might be created.

By using a heavy metal—(such as cadmium, cobalt, chromium) inducible or hormone—(such as estrogen, androgen or other steroid hormone) inducible promoter, a biosensor system might be developed for monitoring environmental pollution and for evaluating water quality for human consumption and aquacultural uses. In such a biosensor system, the transgenic fish would glow with a green fluorescence (or other color depending on the fluorescence protein gene used) when pollutants such as heavy metals and estrogens (or their. derivatives) reached a threshold concentration in an aquatic environment. Such a biosensor system had advantages over classical analytical methods because it is rapid, visualizable, and capable of identifying specific compounds directly in complex mixture found in an aquatic environment, and is portable or less instrument dependent. Moreover, the biosensor system also provided direct information on biotoxicity and it is biodegradable and regenerative.

Environmental monitoring of several substances could be accomplished by either creating one transgenic fish having genes encoding different colored fluorescent proteins driven by promoters responsive to each substance. Then the particular colors exhibited the fish in an environment could be observed. Alternatively, a number of fish can be transformed with individual vectors, then the fish could be combined into a population for monitoring an environment and the colors expressed by each fish observed.

In addition, the fluorescent transgenic fish should also be valuable in the market for scientific research tools because they could be used for embryonic studies such as tracing cell lineage and cell migration. Cells from transgenic fish expressing GFP could also be used as cellular and genetic markers in cell transplantation and nuclear transplantation experiments.

The constructs two fluorescent genes demonstrated successfully in zebrafish in the present invention should also be applicable to other fish species such as medaka, goldfish, carp including koi, loach, tilapia, glassfish, catfish, angel fish, discus, eel, tetra, goby, gourami, guppy, Xiphophorus (swordtail), hatchet fish, Molly fish, pangasius, etc.

What is claimed is:

1. A recombinant plasmid, comprising:
    (a) a α-actin promoter operably linked to a gene encoding a red-fluorescent protein; and
    (b) a β-actin promoter operably linked to a gene encoding a green fluorescent protein; wherein the α-actin promoter and the β-actin promoter have an adverse directional transcription property.

* * * * *